United States Patent [19]

Gagne

[11] Patent Number: 5,456,125
[45] Date of Patent: Oct. 10, 1995

[54] MEMBRANE CUTTER AND RETRIEVER

[75] Inventor: Helen M. Gagne, Dracut, Mass.

[73] Assignee: Millipore Corporation, Bedford, Mass.

[21] Appl. No.: 221,141

[22] Filed: Mar. 31, 1994

[51] Int. Cl.$^6$ ............................................. G01N 1/08
[52] U.S. Cl. ............................................. 73/864.44
[58] Field of Search ........................ 73/863.23, 864.41, 73/864.44, 864.45; 83/919

[56] References Cited

U.S. PATENT DOCUMENTS

| | | | |
|---|---|---|---|
| 3,495,488 | 2/1970 | Addis et al. | 83/919 |
| 4,754,655 | 7/1988 | Parker, III et al. | 73/863.23 |
| 5,245,878 | 9/1993 | Underwood | 73/864.44 |

FOREIGN PATENT DOCUMENTS

| | | | |
|---|---|---|---|
| 312133 | 8/1971 | U.S.S.R. | 73/864.44 |

*Primary Examiner*—Robert Raevis
*Attorney, Agent, or Firm*—Andrew T. Karnakis

[57] ABSTRACT

A membrane cutter and retriever is disclosed which includes a hollow circular die securely fastened through a hollow connector to the luer opening of a syringe. The die/syringe assembly is inserted within a filter holder unit having a membrane secured to the bottom thereof. The die contacts the periphery of the membrane and is rotated to cut and release the membrane from the holder unit. The plunger of the syringe is then raised to create a vacuum which forces the cut membrane into the hollow die where it is retained until such time as the plunger is lowered to create sufficient pressure to deposit the membrane at a desired location for subsequent analysis.

8 Claims, 1 Drawing Sheet

MEMBRANE CUTTER AND RETRIEVER

BACKGROUND OF THE INVENTION

This invention relates to an apparatus for cutting and retrieving a porous membrane which is securely fastened to a membrane holder.

Porous membranes housed in secure fashion to rigid holders are widely used in many applications in which a sample solution is contacted with the surface of the membrane. Solutes of interest in the sample are captured on or bound to the surface of the membrane. Thereafter it is often desirable to remove the membrane from its holder and subsequently transport it to another location or device for further analysis.

In analytical techniques involving biomolecules, such as proteins or peptides, the researcher is often working with small quantities of expensive samples (particularly in terms of time and effort to produce and/or purify). Thus disruption of the membrane-containing sample must be kept to a minimum to avoid contamination which could skew the results of any subsequent analysis/processing of the sample or, worse yet, destroy the biomolecular sample under investigation.

The difficulties associated with the foregoing techniques become exacerbated when samples are filtered inside a centrifuge. In this instance, the sample is added to an elongated plastic container having a membrane securely fastened at the bottom of the container. Often the membrane is supported on its downstream side by an additional rigid plastic screen. Thus removal of the membrane from devices of this type has heretofore involved cutting away the plastic housing which holds the membrane with razor blades or clippers, a cumbersome and, in the case of razors, a potentially harmful alternative. Furthermore, once removed, the membrane must be handled either with forceps or other mechanical means to transport the cut membrane for subsequent analysis or processing. Additionally, it may be necessary to perform a secondary cut to trim the membrane such that only the active filter area is presented for analysis. Such manipulations can seriously degrade the sample to be analyzed.

The prior art includes numerous examples of cutters or punches used to separate a porous membrane from its holder device. For example, U.S. Pat. No. 5,146,794 describes a filter punch particularly useful for multi-well plates. While the punch described in the '794 patent represented a significant advance, membranes located at the base of multi-well plates are generally unsupported and easily accessible. In addition, this patent discloses a punch with a protruding member with a sharp point which pierces the center of the membrane. This impacts the useful filtration area of the membrane which can be a problem when dealing with small quantity biomolecule samples such as peptides.

An example of a centrifugal filter unit is the Prospin™ Sample Preparation Cartridge sold by Applied Biosystems, Inc. In this unit, a membrane is secured inside the bottom of an elongate container (termed an insert) without a rigid support on its downstream side. After filtration, the insert is inverted, fully exposing the membrane. A punch is placed on the downstream side of the membrane and pushed down to cut the membrane around the periphery of the insert causing it to separate from the insert. This technique can expose the membrane to contaminants and also requires that the membrane be retrieved with a secondary tool such as forceps.

Accordingly, it would be desirable to provide a device capable of cutting a membrane and retrieving the cut membrane in one operation with minimal chance of contaminating or otherwise compromising the sample to be analyzed. It would also be advantageous for such a device to function with both supported and unsupported membrane holder devices.

SUMMARY OF THE INVENTION

The present invention overcomes the limitations and disadvantages of the prior art by offering a device which greatly facilitates the cutting and retrieval of a porous membrane securely fastened to a holder. Significantly, membrane retrieval is accomplished as part of the same operation as the cutting of the membrane from the holder in a manner which minimizes the chances for disrupting the membrane surface and compromising samples on the membrane surface.

In accordance with a preferred embodiment, a cutter appropriately sized to correspond to the membrane area to be cut includes a die with a circular cutting edge and a hollow passage which extends axially throughout the length of the die. The die is securely fastened via a hollow metal connector to the luer opening of a conventional syringe. The syringe/cutter assembly is inserted within a membrane filter holder such that the die contacts the porous membrane which is supported on its downstream side by a rigid plastic screen. With the plunger of the syringe depressed, the cutter is rotated by turning the syringe to cut the membrane from the holder. The plunger is then raised to create a vacuum which forces the cut membrane into the hollow passage where it is retained until the plunger is lowered to create sufficient pressure to deposit the membrane at a desired location (e.g. Petri dish, test tube, etc.) for subsequent analysis.

Alternatively, the same device may be used to cut and retrieve membranes that are used with unsupported membrane filter holder units. In this instance, the filter holder can be placed with the membrane down on a smooth, clean solid surface. The cutter is inserted as discussed above and the top of the syringe is tapped to cut the membrane from the holder. Thereafter the same procedure is followed to create a vacuum to retrieve the membrane and transport it to a desired location.

The present invention thus eliminates the use of dangerous razor blades and secondary tools for handling the cut membrane, thereby minimizing the chances for contamination of the sample to be analyzed. The cutter can be readily cleaned after each operation to avoid cross contamination. Moreover, the device is easily adapted to other membrane sizes and designs by simply making dimensional modifications to the cutter and connector.

These and other advantages of the present invention will become apparent from the following detailed description of the invention taken together with the accompanying figures.

DETAILED DESCRIPTION OF THE INVENTION

Figure 1:
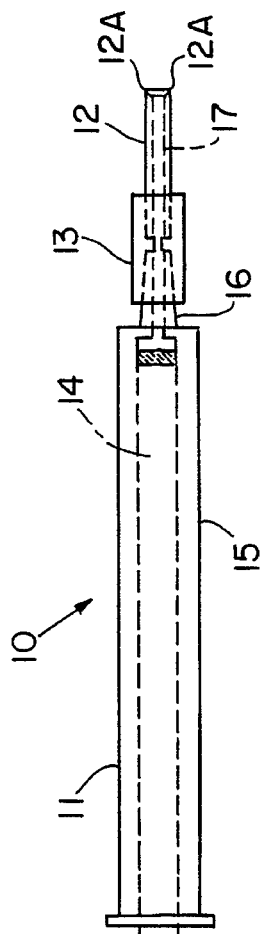
FIG. 1 is a schematic view in cross section of a membrane cutter and retriever constructed in accordance with a preferred embodiment of the present invention.
Figure 2:
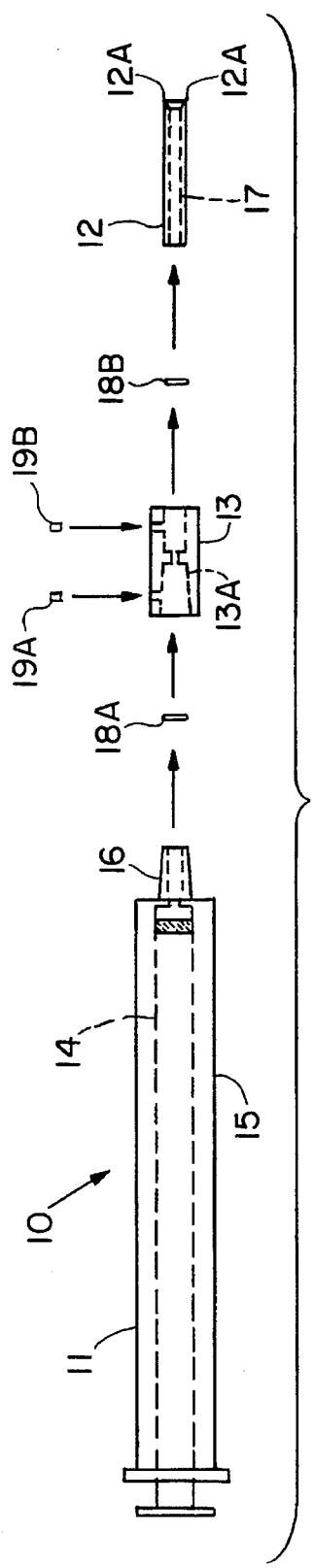
FIG. 2 is an exploded view showing details of the assembly of the embodiment of FIG. 1.

Turning to FIGS. 1 and 2, there is shown a membrane cutter and retriever 10 which includes a syringe 11 and a tubular cutting die 12 joined together by a hollow connector 13. The syringe is conventional and contains a plunger 14 which in known fashion sealingly rides "up and down" (left and right as shown in the drawing orientation) within an outer concentric tube 15 to alternatively create a vacuum on the up stroke and a pressure on the down stroke. The syringe also includes a standard slip fit luer end 16 for interfacing with other instrumentalities, most often a needle, but in this instance the connector 13.

The die 12 is formed of a hardened steel and includes an internal passage 17 which axially extends throughout its length and terminates at one end in a circular cutting edge 12A. The connector 13 joins the die to the syringe 11. The connector preferably is a hollow metal sleeve with one end 13A tapered (see FIG. 2) to conform to the luer end 16 of the syringe so as to form a reliable joint between the two to prevent independent rotation of the die and syringe when cutting membrane as will be explained presently below. A pair of O-ring gaskets 18A, 18B are used at each connection (i.e. between each end of the connector and the syringe and the die respectively) to prevent air leakage and thus enhance the vacuum producing capability of the cutter and retriever 10. To complete the assembly, set screws 19A, 19B fixedly join the connector to the syringe and to the die. As will be appreciated an air passage from the luer end of the syringe through the hollow connector and the hollow die up to its cutting edge has been maintained as indicated by the dashed lines in FIG. 1.

Figure 3:
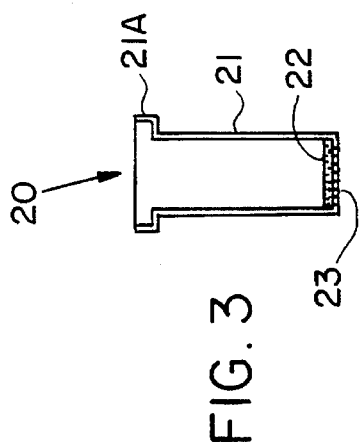
FIG. 3 is a schematic diagram in cross section of a membrane filter holder unit useful with the cutter and retriever of FIG. 1.

The operation of the cutter and retriever 10 will be illustrated in the context of a membrane filter holder unit 20 shown in FIG. 3. Units of this type are adapted for centrifugal filtration of biomolecules such as peptides and are commercially available from a number of vendors. One such product is the Ultrafree® MC Filter Unit sold by Millipore Corporation. The unit 20 includes an elongate cylindrical cavity 21 with an enlarged upper lip 21A for receiving and for holding sample. Securely attached to the base of the cavity is a porous membrane 22 suitable for retaining the sample of interest on its surface, such as the Immobilon™ SQC membrane available from Millipore. The downstream side of the membrane is supported by a rigid plastic screen 23 which is formed in the bottom of the cavity 21.

After the sample is filtered, as for example with the aid of a centrifuge (not shown), the filter holder unit 20 is removed from the centrifuge. To remove the membrane 22, the die 12 is inserted in the filter unit, with the plunger 14 of the syringe 11 depressed, until the die contacts the membrane. The die, which is sized such that the diameter of the cutting edge is slightly smaller than the internal diameter of the cylindrical cavity 21, is then rotated to cut the membrane to release it from the filter holder unit. Vacuum is applied by raising the plunger and the membrane is mechanically held inside the passage 17. To release the membrane after it is transported to a desired location for further analysis, as for example to a test tube or Petri dish, the plunger is depressed thereby creating a pressure sufficient to dispense the membrane.

The cutter and retriever 10 works equally well with filter units that are not supported on the downstream side of the membrane as with the Prospin cartridge discussed previously. In this instance, after filtration has been completed the unit is placed membrane side down on a smooth surface which has been preferably cleaned with an appropriate agent to prevent sample contamination. The die 12 is inserted until the membrane 22 is contacted and the top of the syringe 11 (with plunger 14 fully depressed) is tapped with a mallet or other suitable blunt object to cut the membrane about its periphery adjacent to the inner walls of filter holder 20 thereby freeing the membrane from the holder. Thereafter vacuum is applied as discussed above and the membrane is retained in the die, transported and dispensed at a desired location by lowering the plunger as before.

Other modifications are apparent without departing from the scope of the present invention. For example, other devices such as a rubber bulb could be substituted for the syringe. In addition, the principles of membrane retrieval described herein can be extended to automated handling of a multitude of samples as opposed to the individual hand held apparatus described above. In automated operation, a plurality of cutter dies may be assembled in a work station under the control of a robotic system, with each die being connected via appropriate tubing to a manifold, which in turn is in fluid communication with a vacuum source such as a pump. The dies are rotated robotically to cut the membrane from the holder, vacuum is applied to remove and retain the membrane, the die with its retained membrane is transported to a desired location, and a pressure pulse releases the membrane from the die.

The foregoing description is merely for purposes of illustration and the present invention is not to be limited thereby, but only in accordance with the claims set forth below.

I claim:

1. An apparatus for cutting from a membrane holder and retrieving a porous membrane upon which a sample to be analyzed has been retained comprising:

cutter means having a cutting edge suitable for cutting and releasing said membrane from said holder to produce a cut membrane sample, said cutter means including an internal passageway extending substantially perpendicularly from the plane of said cutting edge;

vacuum means connected to said passageway for creating a vacuum therein;

means for applying said vacuum to said passageway such that vacuum forces act directly on said cut membrane sample; and means for retaining said cut membrane sample in said passageway in the vicinity of said cutting edge.

2. The apparatus of claim 1 including means for applying a positive pressure to said passageway to dispense said cut membrane sample from said passageway.

3. The apparatus of claim 2 wherein said means for applying a positive pressure comprises a plunger-activated syringe affixed to said cutter means and in fluid communication with said passageway.

4. The apparatus of claim 1 wherein said cutter means is a tubular die and said cutting edge is circular.

5. The apparatus of claim 4 wherein the diameter of said cutting edge is approximately the same diameter as the useful filtration area of said membrane.

6. The apparatus of claim 5 wherein said cutting edge is inwardly beveled toward said passageway to form a region wherein said cut membrane is retained.

7. The apparatus of claim 6 wherein said vacuum means comprises a plunger-activated syringe affixed to said die with the open end of said syringe being in fluid communication with said passageway.

8. The apparatus of claim 1 wherein said vacuum means comprises a plunger-activated syringe affixed to said cutter means with the open end of said syringe being in fluid communication with said passageway.

* * * * *